US005457252A

United States Patent [19]
Gill et al.

[11] Patent Number: 5,457,252
[45] Date of Patent: Oct. 10, 1995

[54] CATALYST COMPOSITION FOR THE SELECTIVE HYDROGENATION OF BENZENE AND PROCESS FOR SUCH HYDROGENATION

[75] Inventors: Udai S. Gill, Nepean; Craig W. Fairbridge, Kinburn; Brian A. Farnand, Nepean; Esteban C. Castellanos, Kanata, all of Canada

[73] Assignee: Her Majesty the Queen in right of Canada, as represented by the Minister of Energy, Mines & Resources, Canada

[21] Appl. No.: 115,089

[22] Filed: Sep. 2, 1993

Related U.S. Application Data

[63] Continuation-in-part of Ser. No. 801,395, Dec. 2, 1992, Pat. No. 5,254,763.

[51] Int. Cl.[6] ............................ C07C 5/10; C07C 13/465; C07C 7/10; C07C 7/152
[52] U.S. Cl. ............................ 585/269; 585/266; 585/841; 585/850; 208/143; 208/144; 208/264
[58] Field of Search ............................ 585/266, 269, 585/841, 850; 208/143, 144, 264

[56] References Cited

U.S. PATENT DOCUMENTS

| | | | |
|---|---|---|---|
| 3,113,986 | 12/1963 | Breslow et al. | 585/266 |
| 3,912,787 | 10/1975 | Nowack et al. | 585/269 |
| 4,197,415 | 4/1980 | Hideyuki et al. | 585/269 |
| 4,645,849 | 2/1987 | Lewis | 585/266 |
| 4,678,861 | 7/1987 | Mitsui et al. | 585/266 |
| 4,783,565 | 11/1988 | Naruse et al. | 585/268 |
| 5,254,763 | 10/1993 | Gill et al. | 585/269 |

Primary Examiner—Sharon A. Gibson
Assistant Examiner—E. D. Irzinski
Attorney, Agent, or Firm—Nixon & Vanderhye

[57] ABSTRACT

A novel catalyst has been provided for the selective hydrogenation of benzene in gasoline. The catalyst mixture comprises a water-soluble, organo-metallic, selective benzene hydrogenation catalyst comprising catalytically-active mixture of (A) $M[L]_x[X]_y$ wherein M is a metal selected from the group consisting of Cr, Fe, Co, Ni, Mo, Ru, Rh, Pd, Ta, W, Re, Os, Ir, Pt, La and Ce; L is an aromatic hydrocarbon, e.g., benzene, diphenyl, etc., or a diaromatic hydrocarbon, e.g., naphthalene; X is a halogen; x is an integer from 1 to 10 inclusive; and y is an integer from 1 to 10 inclusive; and (B) tris(triphenylphosphine)rhodium(I)halide or tris(triphenylphosphine)ruthenium(I)halide. In use the process comprises admixing the gasoline with water. The above-identified water-soluble, organo-metallic selective benzene hydrogenation catalyst mixture is then added. A catalytic hydrogenation is then carried out in a hydrogenation zone at a temperature of about 150° to about 245° C. at a pressure of up to about 1000 psi in a hipbasic system of the water and the gasoline. The benzene is selectively solubilized in the water and thus is selectively hydrogenated in the presence of the above-identified water soluble organo-metallic catalyst mixture. The gasoline is then recovered from the hydrogenation zone. This combination of both catalysts was found to produce conversions in excess of 40% which was much greater than either of the catalysts separately and at the lowest effective temperature of 150° C.

11 Claims, 3 Drawing Sheets

CATALYST COMPOSITION FOR THE SELECTIVE HYDROGENATION OF BENZENE AND PROCESS FOR SUCH HYDROGENATION

BACKGROUND OF THE INVENTION (i) Related Applications

This application is a continuation-in-part of U.S. patent application Ser. No. 07/801,395 filed Dec. 2, 1991, the entire contents of which are incorporated herein by reference.

(ii) Field of the Invention

This invention relates to a process and catalyst composition for selectively removing benzene from gasoline.

(iii) Description of Prior Art

Hydrogenation is used to increase the quality of some fuels, because olefins and unstable species produce gums. Even when high octane aromatics are desirable, some of them, like benzene, are being regulated.

In response to environmental concerns and anticipating future EPA requirements, petroleum refiners must reduce the benzene content of their gasoline. This increases the expense of producing gasoline as well as decreasing its quality.

The metals normally used according to their activity for hydrogenation are:

For Ethylene Rh>Pd>Pt>Ni>Fe>W>Cr>Ta

For Acetylene Pd>Pt>Ni,Rh>Fe,Cu,Co,Ir>Ru,Os

For Isoprene Pd>Ni>Co

For Benzene Pt,Rh,Ru>Ni>Pd

The catalyst type varies according the feedstock and process used, but normally the most employed types are three: supported catalysts, mass catalysts and soluble catalysts. The metals employed for supported catalysts are mostly Ni, Pd, Pt on alumina or silica, Ni-Mo and Ni-W sulphides on alumina. The mass catalysts are usually nickel in tablets like Raney Nickel, whereas the soluble catalysts more used are the alkanoates together with organometallic reducing agents.

The interest for homogeneous catalysts in hydrogenation of organic compounds comes from the fact that many of them are highly selective and produce good yields. The major breakthrough in this field was the synthesis of an active rhodium complex, namely, tris(triphenyl-phosphine)rhodium(!)chloride (partially soluble in water and in gasoline) and the corresponding ruthenium complex, namely, tris(triphenylphosphine)ruthenium(I)chloride by Wilkinson and co-workers in 1965. In 1967, Winkhaus and Singer synthesized a water soluble hexacoordinated benzene organometallic complex, namely, $RuC_6H_6Cl_2$, (Organometal. Chem., 7 (1967) 487).

While the Wilkinson catalyst described above is a widely used catalyst for homogeneous hydrogenation, the Winkhaus and Singer catalyst is a less known compound, reported as an homogeneous catalyst for the hydrogenation and isomerization of olefins, namely, 1-pentene, 2-pentene, 1-hexene and cyclooctene, in the presence of a base, e.g., triethylamine and pyrrolidine in polar coordinating solvents. It is also known that cycloolefins and quino-lines can be hydrogenated to corresponding cycloalkanese and tetrahydroquinolines in the presence of a base under mild conditions.

At the present time, there is environmental pressure to remove benzene, a suspected carcinogen, from gasoline. Technologies, e.g., liquid-liquid extraction, or conventional hydrogenation, are presently available. However, the former may be too expensive for low quantities of benzene, and the latter may eliminate all the aromatic components, with significant loss of octane number.

Several methods have been proposed for reducing benzene in gasoline to respond to the new legislation. Usually the processes for benzene reduction include two steps, i.e., separation of the benzene, followed by either direct utilization of the benzene or its conversion. The alternatives included (1) distillation of naphtha and reformate to produce a concentrated benzene stream and (2) removal of benzene precursors ($C_6$ naphthenes) from feedstock prior to reforming. The concentrated benzene streams could be either hydrogenated to produce cyclohexane or extracted to produce pure benzene for sale. Alkylation of streams containing benzene may be achieved using methanol, ethanol or propylene on ZSM-5 zeolite and other acidic catalysts.

In the patent literature, U.S. Pat. No. 3,767,720 described the hydrogenation of a pure stream of liquid aromatic in the presence of an aqueous stream of reduced Group VIII cations, including ruthenium. Such process was carried out under the condition of high pH and in the presence of a reducing agent in the aqueous phase to convert the Group VIII cations to neutral species. The source of the Group VIII cations was inorganic salts. This provided a process for producing cyclohexane from benzene using a catalyst comprising a reduced cation of a Group VIII element, i.e., in an aqueous solution of, e.g., $Zn^{+++}$, $Cr^{++}$, $Hg^+$, $Hg^{++}$, $Ni^{++}$, $Mo^{++}$, $Fe^{++}$, $Fe^{+++}$, $Co^{++}$, or $Cu^+$.

U.S. Pat. No. 3,274,272 patented Sep. 20, 1966 by M. Amagasa et al, described unusual liquid ammonia complexes with pure aromatic components with thermal decomposition of the ammonia, partly to saturate the aromatic component along with aqueous/metallic Group IA metals to reduce the benzene ammonia complex. It provided a process for producing cyclohexane from benzene using an alkali metal or alkaline earth metal dissolved in liquid ammonia in the presence of a decomposing agent.

U.S. Pat. No. 4,271,323 patented Jun. 2, 1981 by Durand et al, indicated that some homogenous catalysts can be used for hydrogenation of benzene as well as other components. It provided a process for hydrogenating benzene in the liquid phase in the presence of a particularly reacted soluble catalyst.

The above-identified co-pending application of which the present invention is a continuation-in-part, provided a process for the selective hydrogenation of benzene in an organic solution of other organic hydrocarbon compounds. The process involved admixing the solution with water. A water-soluble organo-metallic hydrogenation catalyst was added to that solution. A catalytic hydrogenation was carried out in a hydrogenation zone at a temperature of about 45° to about 250° C. at a pressure of about 200 psi to about 500 psi in a biphasic system of the water and the organic solution. In such a reaction, the benzene was selectively solubilized in the water and thus was selectively hydrogenated in the presence of the water soluble organo-metallic catalyst. The organic solution was then recovered from the hydrogenation zone.

SUMMARY OF THE INVENTION i) Aims of the Invention

The prior art is thus deficient in any commercially-feasible teaching of selectively removing benzene from gasoline or other solutions of benzene in hydrocarbon.

Accordingly, it is an object of this invention to provide a process for selectively hydrogenating benzene in a mixture of gasoline and other aromatic compounds.

Another object of this invention is to provide a catalyst composition for the selective hydrogenation of benzene in a mixture of gasoline and other aromatic organic compounds.

(ii) Statement of Invention

Of the components found in gasoline, only the aromatics have significant water solubility. Further, benzene is approximately 3.5 times more soluble than toluene, which is approximately 2.5 times more soluble than the xylenes. It is thought that this water solubility can be exploited to perform the selective hydrogenation of benzene to cyclohexane without affecting toluene or xylenes. The present invention takes advantage of this to provide a low cost of operation, selective benzene hydrogenation, with no significant loss of octane number.

The present invention therefore provides a process for the selective hydrogenation of benzene in an organic solution of other organic hydrocarbon compounds, (e.g., gasoline), the process comprising: admixing the organic solution with water; adding a water-soluble organo-metallic hydrogenation catalyst mixture comprising catalytically-active mixture of (A) $M[L]_x[X]_y$, wherein M is a metal selected from the group consisting of Cr, Fe, Co, Ni, Mo, Ru, Rh, Pd, Ta, W, Re, Os, Ir, Pt, La and Ce; L is an aromatic hydrocarbon, e.g., benzene, diphenyl, etc. or a diaromatic hydrocarbon, e.g., naphthalene; X is a halogen; x is an integer from 1 to 10 inclusive; and y is an integer from 1 to 10 inclusive; and (B) a tris(triphenylphosphine)rhodium(I)halide or a tris(triphenylphosphine)ruthenium(I)halide; catalytically hydrogenating the benzene in a hydrogenation zone at a temperature of about 150° to about 245° C. at a pressure of up to about 1000 psi in a hipbasic system of the water and the organic solution, whereby selectively to solubilize the benzene in the water and thus selectively hydrogenating the benzene in the presence of the water soluble organo-metallic hydrogenation catalyst mixture; and recovering the organic solution from the hydrogenation zone.

This invention also provides a selective hydrogenation catalyst comprising an aqueous solution of a water-soluble, organo-metallic hydrogenation catalyst mixture comprising catalytically-active-mixture of (A) $M[L]_x[X]_y$, wherein M is a metal selected from the group consisting of Cr, Fe, Co, Ni, Mo, Ru, Rh, Pd, Ta, W, Re, Os, Ir, Pt, La and Ce; L is an aromatic hydrocarbon, e.g., benzene, diphenyl, etc., or a diaromatic hydrocarbon, e.g., naphthalene; X is a halogen; x is an integer from 1 to 10 inclusive; and y is an integer from 1 to 10 inclusive; and (B) a tris(triphenylphosphine)rhodium(I)halide or a tris(triphenylphosphine)ruthenium(I)halide.

(iii) Other Features of the Invention

By preferred features of this invention, the aromatic hydrocarbon is benzene or diphenyl, or the diaromatic hydrocarbon is naphthalene.

In one feature of the process of this invention, mixture (A) in the catalytically-active mixture comprises a compound of the formula $M'[L']_a[X']_b$, wherein M' is a metal selected from the group consisting of Pt, Rh, Ru, N, and Pd; L' is $C_6H_6$; X' is Cl or Br; x' is 1; and y' is 2.

In another feature of the process of this invention, the hydrogenation catalyst is a catalytically-active mixture of (A) $Ru[C_6H_6]Cl_2$ and (B) tris(triphenylphosphine)rhodium(I)-chloride.

In yet another feature of the process of this invention, the hydrogenation catalyst is a catalytically-active mixture of (A) $Ru[C_6H_6]Cl_2$ and (B) tris(triphenylphosphine)ruthenium(I)chloride.

In another feature of the process of this invention, the ratio of (A) to (B) in the catalytically-active mixture is from about 1000 parts (A) to 1 part (B) to 1 part (A) to about 1000 parts (B). In a more specific feature of this process, such ratio is from about 1 part (A) to about 1 part (B).

In other features of the catalyst of this invention, (B), in the catalytically-active mixture may comprise tris(triphenylphosphine)rhodium(I)chloride; or catalyst (B) may comprise tris(triphenylphosphine)ruthenium(I)chloride.

In yet another feature of the catalyst of this invention, the hydrogenation catalyst is a catalytically-active mixture of (A) $Ru[C_6H_6]Cl_2$ and (B) tris(triphenylphosphine)rhodium(I)chloride.

In a still further feature of the catalyst of this invention, the hydrogenation catalyst is a catalytically-active mixture of (A) $Ru[C_6H_6]Cl_2$ and (B) tris(triphenylphosphine)ruthenium(I)chloride.

In another feature of the catalyst of this invention the ratio of catalyst (A) to catalyst (B) is from about 1000 parts (A) to 1 part (B) to 1 part (A) to about 1000 parts (B). In a more specific feature of this catalyst, such ratio is about 1 part (A) to about 1 part (B).

iv) Generalized Description of the Invention

There are thus two major features to the present invention. The first is the unique hydrogenation catalyst mixture. The second feature is the selective hydrogenation of benzene in competition with other aromatic, organic compounds, including toluene and/or xylene. Since benzene has been identified as undesirable in gasoline for health reasons, it is commercially very attractive to remove the benzene from gasoline without affecting the benign high performance aromatic organic compounds.

In addition, a third advantageous feature of this invention is that there is no loss of catalyst mixture since the catalyst mixture may be recycled in the aqueous phase.

BRIEF DESCRIPTION OF THE DRAWINGS

In the accompanying drawings.

DESCRIPTION OF THE PREFERRED EMBODIMENTS

Figure 1:
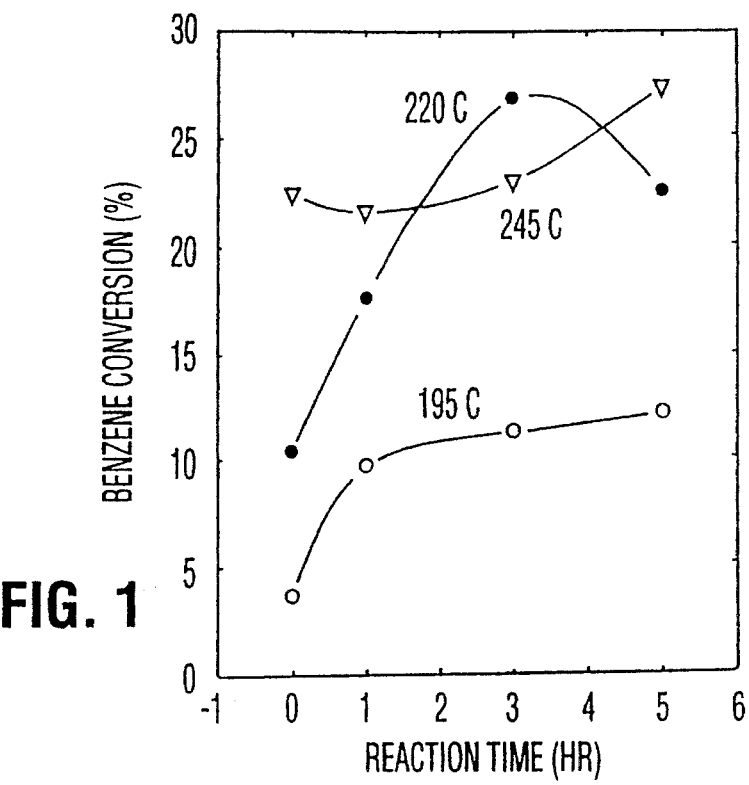
FIG. 1 is a graph of benzene conversion (%) as ordinate and reaction time (hrs) or abscissa showing the effect of reaction temperatures.

The following are Examples of the process of this invention. Before describing the Examples, the following additional information is provided.

Several chemicals were required to synthesize the catalyst: Ruthenium (III) chloride hydrate (RuCl$_3$.3H$_2$O) and 1,4-cyclohexadiene, 97% stabilized with 0.1% hydroquinone were obtained from Aldrich Chem. Co. Ethyl alcohol reagent and spectrophotometric grade methyl alcohol, were purchased from Sigma Chem. Co. Gases used for the reaction experiments and the gas chromatography analysis were ultra high purity helium, ultra zero hydrogen, ultra zero nitrogen and ultra zero argon obtained from Praxair. Tris-(triphenylphosphine)rhodium(I) chloride (Wilkinson catalyst) was obtained from Caledon Laboratories Ltd.

Experiment 1

Gasoline Feedstock

The unleaded gasoline feedstock was obtained from a commercial gasoline distribution center. Nitrogen was bubbled through the gasoline for three hours to strip it some of its light components prior to use in the hydrogenation experiments.

Experiment 2

Catalyst Preparation

The synthesis of [RuC$_6$H$_6$Cl$_2$]$_n$ was performed using the method of Winkhaus and Singer [G. Winkhaus, H. J. Singer, Organometal. Chem, 7 (1967) 487]. RuCl$_3$.xH$_2$O was reacted with 1,3-cyclohexadiene in ethanol at 35° C. The red solution became clear and a precipitate separated from the solution. The brown complex was washed with methanol and dried under high vacuum. Its decomposition point is known to be 200° C. The precipitated complex had the following characteristics: It was soluble in dimethylsulfoxide and insoluble in benzene and chloroform. Infra-red spectroscopy showed C-H valence vibrations bands at 3045 and 2913 cm$^{-1}$. H$^1$ NMR spectroscopy showed only a resonance at $\tau$=3.96 ppm which is attributed to the protons in benzene.

The Wilkinson catalyst was used as received, avoiding contact with air or light. For this purpose, a gas chamber with argon gas used to put the catalyst inside the reactor.

Experiment 3

Analytical Techniques

The feedstock and reactor products were analyzed by gas chromatographic techniques which separated the components. The analytical procedure used here followed a method for petroleum naphtha. This analytical method is comparable to the Canadian Standards method CAN/CGSB-3.0 No. 14.3-M91. The benzene peak is highly resolved and well separated from the others. However, cyclohexane was not observed among the products.

A Varian Vista 6000 chromatograph with a Data Station using a 30 m long DB-1 column, having a 1 µm thick stationary phase was used. The conditions were as follows: The injection volume of the sample was 1 µL. The temperature program consisted of holding at 35° C. for 15 min., 1.5° C./min. to 70° C., 6° C./min. to 130° C., and 8° C./min. to 250° C.

Nuclear magnetic resonance was used to measure the hydrocarbon type distribution including the aromaticity. For these measurements, a Varian XL-300 MHz instrument was used. The sample was mixed with 50% deuterated chloroform. The final spectrum represented an average of 500 scans. The acquisition time was 0.938 s. and the delay between acquisitions was 5 s.

Experiment 4

Cold Model Mixing Studies

In order to study the mixing conditions and to determine the best operating conditions for that purpose, a cold model consisting of a polymethylmethacrylate (PLEXIGLASS™) vessel was built with the same measurements as the reactor, but it was operated at ambient pressure and temperature. The purpose of this experiment was to determine the distribution of the gas phase, the water phase, the gasoline and the catalysts involved in the process regarding the geometrical characteristics of the vessel, the amount of each phase and the stirring rate.

The dimensions of the model were:

Tank height: 9.4 cm

Tank diameter: 5.75 cm

Impeller diameter: 3.92 cm

Volume of reactor: 300 mL

Volume of gasoline: 160 mL

Volume of water: 10 mL

Two catalyst contents were use: 0.1 wt. % and 1 wt. %

In case of the mixing of two catalysts, each represented 1 wt. %.

These mixing studies were performed at ambient conditions in a stirred clear plastic vessel having the same internal dimensions as the high pressure reactor. The solid hydrophylic ruthenium catalyst was contained in the water phase at the bottom of the vessel. The impeller of the mixer was in the organic liquid phase which was between the heavier water phase and the lighter gas phase. At all stirring speeds, a bulk gas phase remained above the two liquid phases. There was no mixing of the four phases at 200 rpm. At 400 rpm some rotational movement of the water phase was apparent, although no mixing of the four phases was observed. At 600 rpm gas bubbles became dispersed throughout all of the organic phase and the upper part of the water phase. However, the bottom 0.5 cm of the water phase did not contain any gas bubbles. At 800 rpm, gas bubbles were dispersed throughout both the organic and water phases. The water and the catalyst remained as a separate phase underneath the organic liquid. At 1000 rpm, some of the water phase was mixed with the organic phase, but 1.5 cm of a dark liquid remained at the bottom of the vessel. At 1400 rpm, water droplets and gas bubbles were dispersed throughout the continuous organic liquid phase. When the mixer was stopped, the liquids separated into two distinct phases immediately. At 1700 rpm, the water droplets and gas bubbles were dispersed throughout the continuous organic liquid phase exactly the same as at 1400 rpm. However, when the mixer was stopped after stirring at 1700 rpm, the organic and aqueous liquids did not separate immediately. They did separate slowly, indicating that a metal stable emulsion had been formed. On the basis of these studies, 1700 rpm was chosen as the mixer speed for the high pressure experiments.

Example 1

Catalytic Reaction

The reactor used in these examples consisted of a 300 mL Parr stirred autoclave having a Parr 4561 assembly system. It included a water cooled packed gland for the stirred seal, a thermocouple and a withdrawal sampling tube for the liquid phase. The reactor had a pressure indicator and a tachometer for measuring the stirrer speed. A proportional, integral, derivative temperature controller was used to regulate the time intervals of the on-off heating system.

Prior to removing liquid samples from the reactor, a vacuum was applied to the sampling lines between the reactor and the sample receiver vessel to remove any liquid remaining from the previous liquid sample. The entire reaction system except the gas cylinders was located inside a fume hood.

In each of the examples, the reactor was loaded with 160 mL of gasoline and 6 mL of a water-catalyst mixture. Water mixtures containing 0.1 and 1.0 wt. % catalyst were used. Air was removed from the reactor by pressurizing and depressing with nitrogen while stirring the reaction mixture. This cycle was repeated twice, then the reactor was pressurized with 0.24 MPa (20 psig) of argon, followed pressurizing with hydrogen to 4.24 MPa (600 psig) or 7.00 MPa (1000 psig).

The reactor was heated to a temperature of either 150° C. (in 15 min) or 195° C. (in 25 min) for the Ru complex. For the Rh complex temperatures of 195°, 220° and 245° C. were used. The conversion which occurred during the heating period was identified as the conversion at time=0. Stirring was stopped while liquid samples of approximately 5 mL were removed at reaction times of 0, 1, 3 and 5 hours.

Specific values for processing conditions were chosen. The following temperatures were used for the Wilkinson catalyst: 195°, 220° and 245° C. For the Ru complex, $RuCl_3$ and mixtures of the two complexes, a temperature of 150° C. was used. Maximum temperatures of 195° C. for the Ru complex and 245° C. were used because it is 5° C. below the catalyst decomposition temperature.

A hydrogen pressure of 1000 psi was selected to keep water and benzene in the liquid state. The stirring rate was 1700 rpm and the catalyst concentration was 1%. Reaction times of 0, 1, 3 and 5 hrs were selected in order to bracket the reaction times used in most industrial processes.

The effect of the reaction temperature on benzene conversion is shown in FIG. 1 for the Wilkinson catalyst. The benzene conversion increased with reaction time at all temperatures from 195° to 245° C. Furthermore, in accordance with normal kinetic phenomena, the benzene conversion increased with increasing temperature. The most significant observation is that the benzene conversions are substantially greater with the rhodium Wilkinson catalyst than those obtained with the ruthenium catalyst as described in the above-identified co-pending application.

Figure 2:
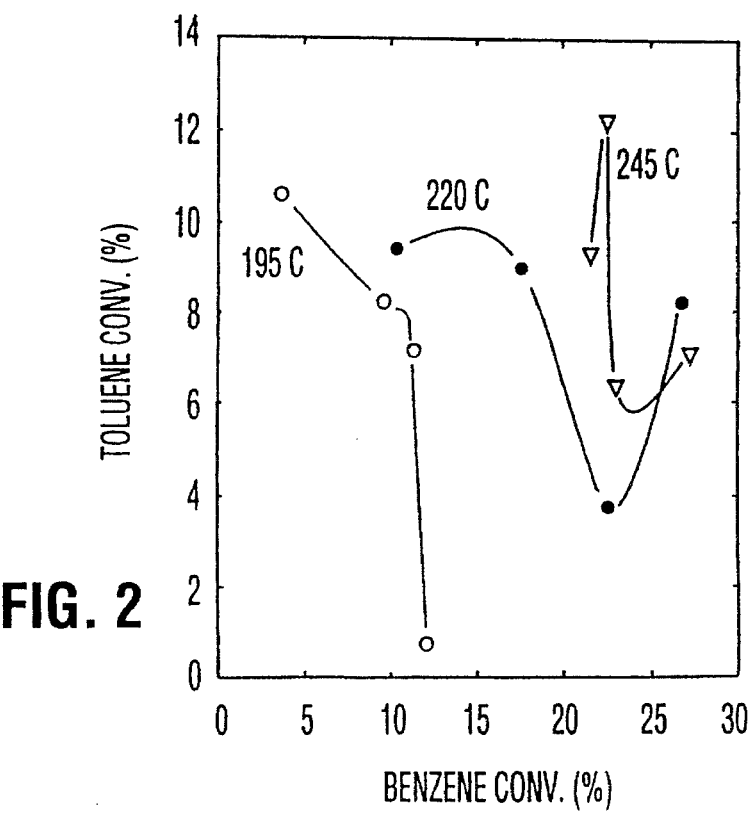
FIG. 2 is a graph of toluene conversion (%) as ordinate and benzene conversion (%) as abscissa showing the effect of temperatures.

Toluene conversion is shown as a function of benzene conversion in FIG. 2. The results with the rhodium catalyst in FIG. 2 show that the benzene conversion at which the toluene conversion decreases becomes greater as the temperature rises. Furthermore, the toluene conversion goes through a minimum as the benzene conversion increases. This minimum toluene conversion increases with reaction temperature. It is desirable to increase the reactor temperature to increase benzene conversion, because environmental considerations have lead to a specification on the maximum quantity of benzene permitted in the gasoline. However, a maximum gasoline specification for toluene does not exist. Therefore, it is desirable to avoid conversion of the high octane toluene. According to the results in FIG. 2, that is achieved by having large benzene conversions at low reaction temperatures.

Figure 3:
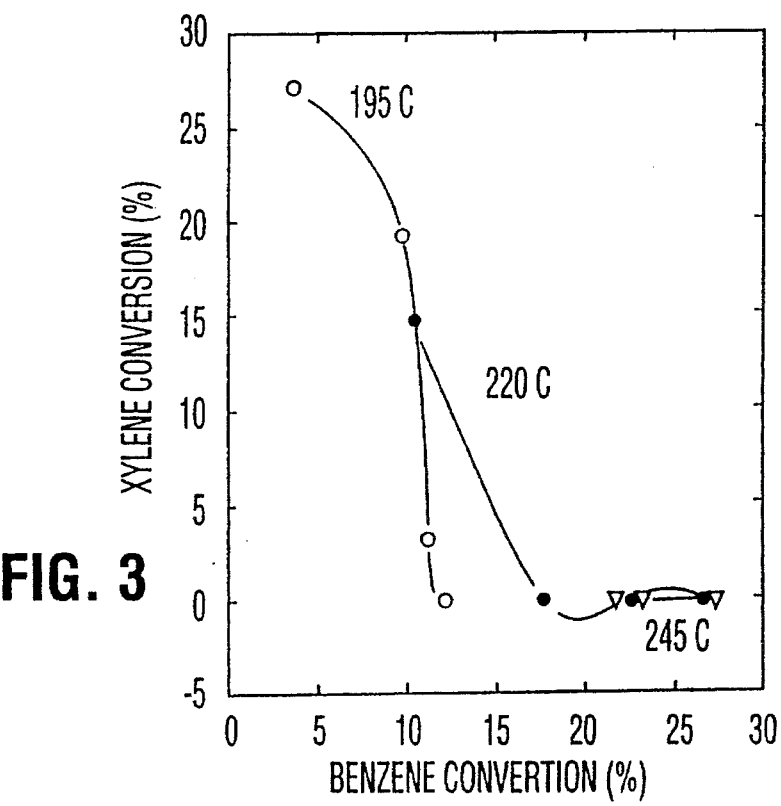
FIG. 3 is a graph of xylene conversion (%) as ordinate and benzene conversion (%) as abscissa showing the effect of temperature.

Xylene conversion is shown as a function of benzene conversion in FIG. 3. In some respect it is similar to the toluene conversion. As the reaction temperature rises, greater benzene conversions are required for the xylene conversion to decrease. However at all reaction temperatures, xylene conversion decreases to zero, if the benzene conversion is large enough.

Figure 4:
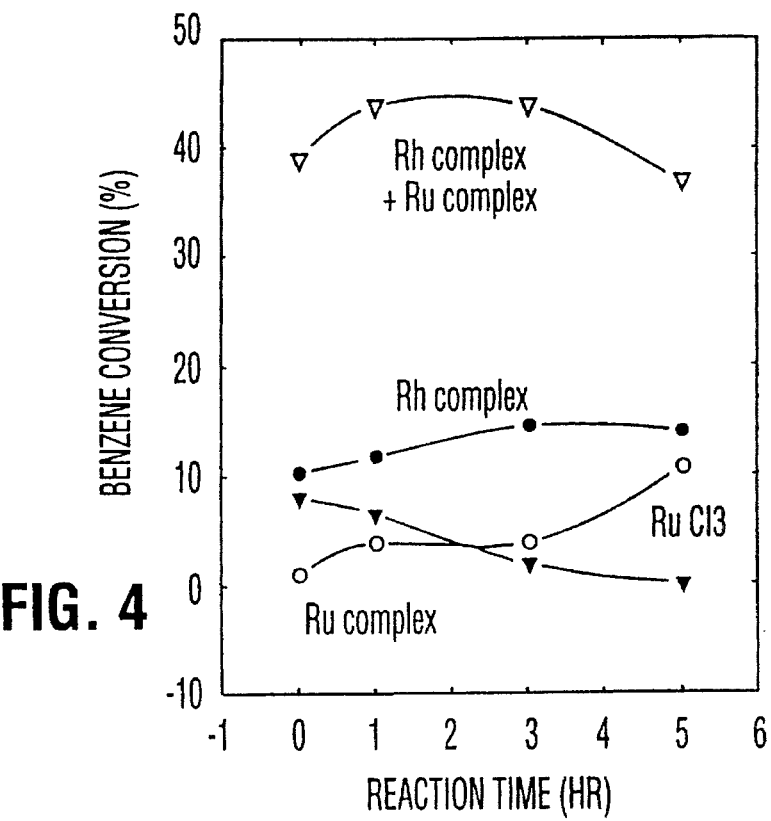
FIG. 4 is a graph of benzene conversion (%) as ordinate and reaction time (hrs) as abscissa for an Pal complex catalyst alone, for an Ru complex catalyst alone and for the combination of an Rh complex catalyst and an Ru complex catalyst.

Benzene conversions obtained with the rhodium Wilkinson catalyst and with ruthenium catalysts of the type described previously in the above-identified co-pending application are shown in FIG. 4 at 150° C., 1000 psi hydrogen and 1700 rpm, 1 wt. % catalyst. Results obtained with a mixture of the rhodium and ruthenium catalysts (1 wt. % each) are also reported. The $RuCl_3$ catalyst and the ruthenium complex catalysts produced similar benzene conversions. The rhodium catalyst produced better results than either of the ruthenium catalysts. However, the mixture of the two catalyst types was far superior than either of the two separately. While it is not desired to be limited to any theory, it is believed that the two catalysts operate by different mechanisms and the combination of the mechanisms is responsible for the synergistic effect.

Figure 5:
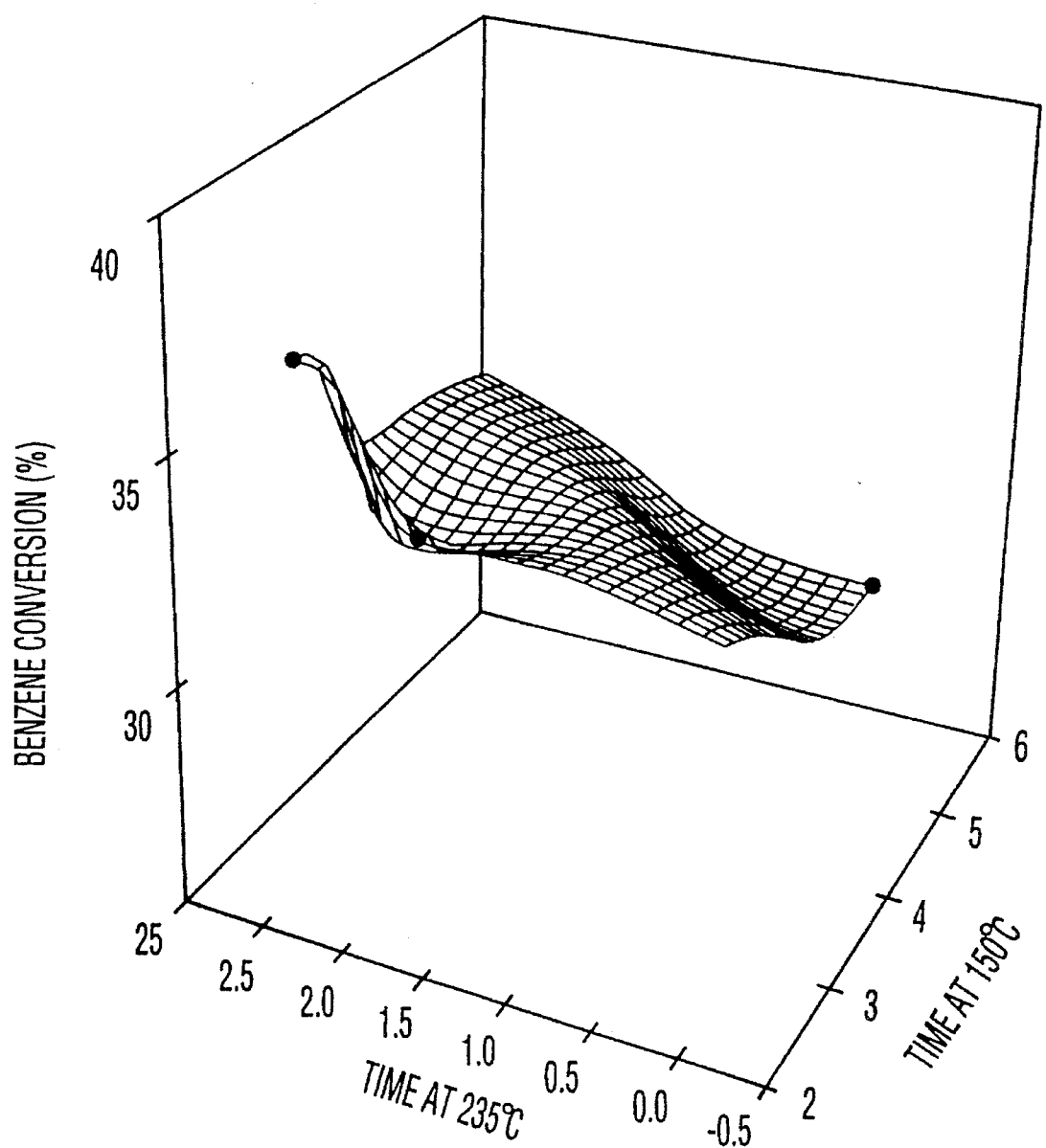
FIG. 5 is a three-dimensional graph of benzene conversion (%)/time at 235° C. and at 150° C.

Conversions from experiments which were performed at a combination of two different temperatures are shown in FIG. 5. The reaction temperature was 150° C. for the first period of time. The second reaction period was at 235° C. The purpose of these experiments was to see the change in benzene conversions by instationary heating periods and to follow the difference in efficiency of the catalyst during these periods of time. It is apparent that the longer the reactor was held at the higher temperature, the greater the benzene conversion.

As described above, the biphasic (aqueous-organic) aqueous catalyst system has a great selectivity for hydrogenating benzene.

This invention can be used as a flexible, low-capital-cost reactor for the removal of carcinogenic suspect benzene from certain gasoline pool streams for which liquid extraction and non-selective hydrogenation are unsuitable. Liquid extraction is unsuitable because of its high cost, while non-selective hydrogenation is unsuitable because of reduction of octane number. Thus, the present invention provides a water soluble reactor system selectively to remove benzene, hydrogenate, and return the cyclohexane product to the gasoline feed stream. Advantages of this process include the use of water selectively to remove benzene, and the use of water selectively to remove benzene, and the use of aqueous soluble catalysts. In addition, the octane quality would be maintained.

The selective hydrogenation of benzene with homogeneous catalyst mixtures is a very interesting way to lower the benzene concentration in the gasoline, according to the new trends to avoid carcinogenic emissions. The advantages include a reduced hydrogen consumption and a controlled reduction of the octane number and an expensive catalyst cost being offset with the implementation of a recycle system or membrane to avoid the loss of the Ruthenium compound.

It is believed that the cost of such hydrogenation treatment would be about 0.54 cents (Canadian)/liter.

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A process for the selective hydrogenation of benzene in an organic solution of other organic hydrocarbon compounds comprising: admixing said solution with water; adding a water-soluble organo-metallic hydrogenation catalyst comprising catalytically-active mixture of (A) $M[L]_x[X]_y$, wherein M is a metal selected from the group consisting of Cr, Fe, Co, Ni, Mo, Ru, Rh, Pd, Ta, W, Re, Os, Ir, Pt, La and Ce; L is an aromatic hydrocarbon or a diaromatic hydrocarbon,; X is a halogen; x is an integer from 1 to 10 inclusive; and y is an integer from 1 to 10 inclusive; and (B) tris(triphenylphosphine)rhodium(I)halide or tris(triphenylphosphine)ruthenium(I)halide; catalytically hydrogenating said benzene in a hydrogenation zone at a temperature of about 150° to about 245° C. at a pressure of up to about 1000 psi in a biphasic system of said water and said organic solution, whereby selectively to solubilize said benzene in said water and thus selectively hydrogenating said benzene in the presence of said water-soluble organo-metallic catalyst; and recovering said organic solution from said hydrogenation zone.

2. The process of claim 1 wherein (A), in said catalytically-active mixture, comprises a compound of the formula $M'[L']_a[X']_b$, wherein M' is a metal selected from the group consisting of Pt, Rh, Ru, N, and Pd; L' is $C_6H_6$; X' is Cl or Br; x' is 1; and y' is 2.

3. The process of claim 1 wherein the ratio of (A) to (B), in said catalytically-active mixture, is about 1000 parts (A) to 1 part (B) to about 1 part (A) to about 1000 parts (B).

4. The process of claim 3 wherein the ratio of (A) to (B), in said catalytically-active mixture, is about 1 part (A) to about 1 part (B).

5. The process of claim 2 wherein (A), in said catalytically-active mixture, comprises $Ru[C_6H_6]Cl_2$.

6. The process of claim 2 wherein (B), in said catalytically-active mixture, comprises tris(triphenylphosphine)rhodium(I)chloride.

7. The process of claim 2 wherein (B), in said catalytically-active mixture, comprises tris(triphenylphosphine)ruthenium(I)chloride.

8. The process of claim 5 wherein (B), in said catalytically-active mixture, comprises tris(triphenylphosphine)rhodium(I)chloride.

9. The process of claim 5 wherein (B), in said catalytically-active mixture, comprises tris(triphenylphosphine)ruthenium(I)chloride.

10. The process of claim 1 wherein said aromatic hydrocarbon is benzene or diphenyl.

11. The process of claim 1 wherein said diaromatic hydrocarbon is naphthalene.

* * * * *